US008999315B2

United States Patent
Henry et al.

(10) Patent No.: US 8,999,315 B2
(45) Date of Patent: Apr. 7, 2015

(54) BIS-QUATERNARY AMMONIUM SALT CORROSION INHIBITORS

(75) Inventors: Kevin M. Henry, Houston, TX (US); Keith D. Hicks, Rosenberg, TX (US)

(73) Assignee: Nalco Company, Naperville, IL (US)

( * ) Notice: Subject to any disclaimer, the term of this patent is extended or adjusted under 35 U.S.C. 154(b) by 2114 days.

(21) Appl. No.: 10/891,575

(22) Filed: Jul. 15, 2004

(65) Prior Publication Data

US 2006/0013798 A1    Jan. 19, 2006

(51) Int. Cl.
    *A61K 31/74*      (2006.01)
    *A61K 31/785*      (2006.01)
    *C09K 8/54*      (2006.01)
    *C23F 11/14*      (2006.01)

(52) U.S. Cl.
CPC ................. *A61K 31/785* (2013.01); *C09K 8/54* (2013.01); *C23F 11/141* (2013.01); *C23F 11/149* (2013.01)

(58) Field of Classification Search
USPC ..................................................... 424/78.09
See application file for complete search history.

(56) References Cited

U.S. PATENT DOCUMENTS

| | | | |
|---|---|---|---|
| 3,424,794 A | 1/1969 | Miller, Jr. et al. | |
| 4,057,390 A | 11/1977 | Quinlan | |
| 4,066,673 A | 1/1978 | Doughty et al. | |
| 4,734,277 A | 3/1988 | Login | |
| 4,778,813 A | 10/1988 | Fenyes et al. | |
| 4,812,263 A * | 3/1989 | Login | 562/114 |
| 4,851,532 A | 7/1989 | Fenyes et al. | |
| 4,970,211 A | 11/1990 | Fenyes et al. | |
| 4,982,000 A | 1/1991 | Earl et al. | |
| 5,300,235 A | 4/1994 | Clewlow et al. | |
| 6,183,550 B1 | 2/2001 | Conner et al. | |
| 6,448,411 B1 * | 9/2002 | Meyer | 548/348.1 |
| 6,559,201 B2 * | 5/2003 | Simendinger, III | 523/122 |
| 6,599,445 B2 | 7/2003 | Meyer | |

FOREIGN PATENT DOCUMENTS

| | | | |
|---|---|---|---|
| EP | 0 535 301 A1 * | 4/1993 | |
| FR | 2718923 | * | 10/1995 |
| JP | 01233264 | * | 9/1989 |
| JP | 01233264 A | * | 9/1989 |
| SU | 688442 A | * | 9/1980 |
| SU | 688442 | * | 9/1990 |

OTHER PUBLICATIONS

Mamada et al. ("Antimicrobial characteristic and adsorption to bacteria of quaternary ammonium salts derived from glycerin" in Res. Dev. Div., Tamura Pharm. Co., Tokyo, 174, Japan; English Abstract).*

Kim et al. (Preparation and Properties of Multiple Ammonium Salts Quaternized by Epicholohydrin in Langmuir, 1996, 12, 6304-6308).*

Dundiene,G.; Yagunova, L.K.; Dauksas, V.; "New Bis-Quaternary Ammonium Salts as Potential Inhibitors of Steel Corrosion", Ukrainskii Khimicheskii Zhurnal (Russian Edition) (1990), 56(3), pp. 295-297 (Abstract).

Mamada, H.; Tagami, Y.; Saito, S.; Yoshimura, J.; "Antimicrobial Characteristics and Adsorption to Bacteria of Quaternary Ammonium Salts Derived from Halogenated Glycerine", Bokin Bobai (1989), 17(9), pp. 413-418 (Abstract).

Mamada, H.; Tagami, Y.; Hoshino, N.; Saito, S.; Yoshimura, J.; "Synthesis and Antimicrobial Characters of Quaternary Ammonium Salts", Bokin Bobai (1989), 17(7), pp. 319-326 (Abstract).

Huilong W.; Jiashen, Z.; Jing L.; "Inhibition of the Corrosion of Carbon Steel in Hydrochloric Acid Solution by Bisquaternary Ammonium Salt", Anti-Corrosion Methods and Materials 49/2 (2002), ISSN: 003-5599 pp. 127-132, (Abstract).

* cited by examiner

*Primary Examiner* — Blessing M Fubara
(74) *Attorney, Agent, or Firm* — Senniger Powers LLP

(57) ABSTRACT

Bis-quaternary ammonium salts of formula $$\left[ R_3R_2R_1\overset{+}{\underset{X^-}{N}}\diagup\diagdown\underset{OH}{\diagup}\diagdown(Y)_n\diagdown\underset{OH}{\diagup}\diagdown\diagup\overset{+}{N}R_4R_5R_6 \right]_p Z^{p-}$$

wherein Y is a group of formula $NR_{11}R_{12}{}^+X^-$ or $NR_7$; n is 0 or 1; p is 1 or 2; r and q are independently 2, 3 or 4; X is an anionic counterion and $R_1R_2R_3N-$ and $R_4R_5R_6N-$ are independently selected from groups of formula $-N(R_{13})_2R_8$, $-N(R_{14})_3$, $-N(R_{13})_3$, $-N(R_{13})_2(CH_2)_qOC(O)R_9$, and $$\underset{R_{10}}{\diagup\diagdown}\underset{}{\overset{N\diagdown\diagup N-R_{11}}{}}$$

wherein $R_7$, $R_{11}$ and $R_{12}$ are independently selected from $C_1$-$C_{18}$ alkyl; $R_8$, $R_9$, $R_{10}$ and $R_{15}$ are independently selected from $C_8$-$C_{18}$ alkyl and $C_8$-$C_{18}$ alkenyl; $R_{13}$ is $C_1$-$C_4$ alkyl; $R_{14}$ is $C_2$-$C_4$ hydroxyalkyl; and $R_{11}$ is selected from $C_2$-$C_4$ hydroxyalkyl, $C_2$-$C_4$ aminoalkyl and groups of formula $-(CH_2)_rNHC(O)R_{15}$ are effective inhibitors of corrosion and biofouling of metallic surfaces in contact with gas- and oil-field fluids.

12 Claims, No Drawings

BIS-QUATERNARY AMMONIUM SALT CORROSION INHIBITORS

TECHNICAL FIELD

This invention relates to use of certain bis-quaternary ammonium salts and compositions for inhibiting corrosion and biofouling of metallic surfaces in contact with corrosive fluids in gas- and oil-field applications.

BACKGROUND OF THE INVENTION

Various systems including oil and gas pipelines, refinery units, cooling systems, steam generators and oil production units in contact with corrosive fluids in gas- and oil-field applications are commonly treated with corrosion inhibitors to preserve metal surfaces, particularly ferrous metal surfaces in contact with the fluids to extend the life of these capital assets. Among the commercially significant classes of corrosion inhibitors are the alkylbenzyldimethylammonium salts containing long chain (>7 carbons) alkyl substituents. Trace concentrations (<250 ppm) of these surfactants have been shown to reduce the corrosion rates of oil-field pipelines.

Likewise, oil and gas pipelines may also be treated with biostatic agents that inhibit the growth of bacteria that colonize within the asset. Among the commercially significant classes of biostatic agents are the alkylbenzyldimethylammonium salts containing long chain (>7 carbons) alkyl substituents. Trace concentrations (<250 ppm) of these surfactants have been shown to reduce the growth of numerous bacterial strains, including the sulfate-reducing bacteria (SRBs). The SRBs reduce sulfate to hydrogen sulfide, which is a highly corrosive substance. The inhibition of SRBs may therefore yield a reduction in the gross corrosion rate of oil and gas pipelines.

Nonetheless, there is an ongoing need for cost- and performance-effective corrosion and biofouling inhibitors for protecting metallic surfaces in oil field systems.

SUMMARY OF THE INVENTION

We have discovered a class of bis-quaternary ammonium salts derived from epihalodrin and tertiary amines which provide superior inhibition of corrosion and biofouling compared to existing treatments derived from quaternary ammonium salts.

Accordingly, this invention is a method of inhibiting corrosion and biofouling of metallic surfaces in contact with a fluid encountered in petroleum operations comprising adding to the fluid an effective corrosion and biofouling inhibiting amount of one or more bis-quaternary ammonium salts of formula

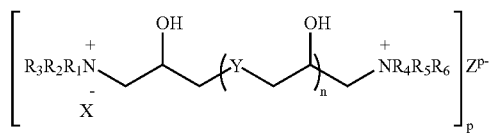

wherein Y is a group of formula $NR_{11}R_{12}^+X^-$ or $NR_7$; n is 0 or 1; p is 1 or 2; r and q are independently 2, 3 or 4; X is an anionic counterion and $R_1R_2R_3N$— and $R_4R_5R_6N$— are independently selected from groups of formula —$N(R_{13})_2R_8$, —$N(R_{14})_3$, —$N(R_{13})_3$, —$N(R_{13})_2(CH_2)_qOC(O)R_9$, and

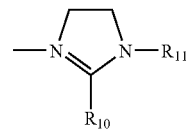

wherein $R_7$, $R_{11}$ and $R_{12}$ are independently selected from $C_1$-$C_{18}$ alkyl; $R_8$, $R_9$, $R_{10}$ and $R_{15}$ are independently selected from $C_8$-$C_{18}$ alkyl and $C_8$-$C_{18}$ alkenyl; $R_{13}$ is $C_1$-$C_4$ alkyl; $R_{14}$ is $C_2$-$C_4$ hydroxyalkyl; and $R_{11}$ is selected from $C_2$-$C_4$ hydroxyalkyl, $C_2$-$C_4$ aminoalkyl and groups of formula —$(CH_2)_rNHC(O)R_{15}$.

DETAILED DESCRIPTION OF THE INVENTION

Definitions of Terms

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, octyl, dodecyl, and the like.

"Alkenyl" means a monovalent group derived from a straight or branched hydrocarbon containing at least one carbon-carbon double bond by the removal of a single hydrogen atom.

"Aminoalkyl" means an alkyl group as defined herein substituted with an an amino (—$NH_2$) group. Representative aminoalkyl groups include 2-aminoethyl, 2- and 3-aminopropyl, and the like.

"Anionic counterion" means the anionic counterion of an organic or inorganic acid neutralizing acid as described herein. The anionic counterion may be organic or inorganic. Repesentative anionic counterions include chloride, fluoride, bromide, iodide, toluenesulfonate, methanesulfonate, sulfate, phosphate, acetate, and the like. Chloride and sulfate are preferred.

"Epihalohydrin" means a compound of formula

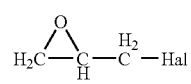

wherein "Hal" is fluorine, chlorine, bromine or iodine. A preferred epihalohydrin is epichlorohydrin.

"Hydroxylalkyl" means an alkyl group as defined herein substituted with a hydroxyl (—OH) group. Representative hydroxyalkyl groups include 2-hydroxyethyl, 2-and 3-hydroxypropyl, and the like.

Preferred Embodiments

The preparation of bis-quaternary ammonium salts suitable for use in the method of this invention is known in the art. See, for example, U.S. Pat. Nos. 4,812,263 and T. S. Kim et al., Langmuir, 1996, 12, 6304-6308.

Bis-quaternary ammonium salts of this invention where n=0 are preferably prepared by dissolving two equivalents of tertiary amine of formula $R_1R_2R_3N$ and $R_4R_5R_6N$ in alcohol or water, or a mixture thereof and neutralizing one such equivalent of tertiary amine with one equivalent of a neutralizing acid. Suitable alcohols include methanol, ethanol, propanol, isopropanol, butanol, isobutanol, ethylene glycol, propylene glycol, and the like. Representative neutralizing acids include HCl, HF, HBr, $H_2SO_4$, $H_3PO_4$, $CH_3CO_2H$, $CH_3SO_3H$, $CH_3C_6H_4SO_3H$, and the like. One equivalent of an epihalohydrin is then added and the resulting mixture is heated at a temperature of about 20 to about 150° C., preferably about 50 to about 100° C. for about 1 to about 30 hours.

Bis-quaternary ammonium salts of this invention where n=1 are preferably prepared by stirring one equivalent of a primary amine of formula $H_2NR_7$ or a secondary amine of formula $HNR_{11}R_{12}$ in alcohol or water, or a mixture thereof as described above and then adding two equivalents of epihalohydrin. The resulting mixture is stirred at ambient temperature for about 1 to about 30 hours. Two equivalents of the tertiary amine of formula $R_1R_2R_3N$ and $R_4R_5R_6N$ are then added and the resulting mixture is heated at a temperature of about 20 to about 150° C., preferably about 50 to about 100° C. for about 1 to about 30 hours.

The groups of formula $R_1R_2R_3N$ and $R_4R_5R_6N$ are independently selected from tertiary amines of formula $N(R_{13})_2R_8$, $N(R_{14})_3$, $N(R_{13})_3$, $N(R_{13})_2(CH_2)_qOC(O)R_9$ and imidazolines of formula

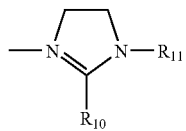

wherein $R_{13}$, $R_{14}$, $R_9$, $R_{10}$, $R_{11}$ and q are defined herein.

Representative amines of formula $H_2NR_7$ include methyl amine, dodecylamine, olelylamine, and the like.

Representative diamines of formula $HNR_{11}R_{12}$ include dimethylamine, diethylamine, didodecylamine, and the like.

Representative tertiary amines of formula $R_1R_2R_3N$ and $R_4R_5R_6N$ include N,N-dimethyldodecylamine, N,N-dimethyloctylamine, N,N-dimethyltetradecylamine, N,N-dimethylhexadecylamine, N,N-olelylamine, triethanolamine, triethylamine, and the like.

Imidazolines suitable for preparing the bis-quaternary salts of this invention are prepared from carboxylic acids of formula $R_{10}CO_2H$ and diamines of formula $H_2NCH_2CH_2NHR_{11}$ under the conditions described in U.S. Pat. No. 6,599,445, incorporated herein by reference.

For example, a representative imidazoline where $R_{10}$ is $C_{17}$ alkyl and $R_{11}$ is —$CH_2CH_2NH_2$ can be prepared by heating one molar equivalent of tall oil fatty acids (TOFA) and about 1.3 molar equivalents of diethylenetriamine (DETA) at about 60° C. to about 225° C. with azeotropic removal of water. Formation of imidazoline is evidenced by removal of the theoretical amount of water and by a strong infrared absorbance at about 1610 cm$^{-1}$ which is indicative of the imidazoline ring.

Imidazolines where $R_{10}$ is $C_{17}$ alkyl and $R_{11}$ is —$CH_2CH_2OH$ can be prepared as described above except substituting 2-(2-aminoethylamino)ethanol (AEAE) for diethylenetriamine. Imidazolines where $R_{10}$ is $C_{17}$ alkyl and $R_{11}$ is —$CH_2CH_2NHC(O)R_{15}$ where $R_{15}$ is $C_{17}$ alkyl can be prepared using about two molar equivalents of TOFA and about one molar equivalent of DETA.

In a preferred aspect of this invention, Y is a group of formula $NR_{11}R_{12}{}^+Cl^-$ or $NR_7$; n is 0 or 1; p is 1 or 2; X is an anionic counterion; and $R_1R_2R_3N$— and $R_4R_5R_6N$— are independently selected from groups of formula —$N(CH_3)_2R_8$, —$N(CH_2CH_2OH)_3$, —$N(CH_2CH_3)_3$, —$N(CH3)_2CH_2CH_2OC(O)R_9$, and

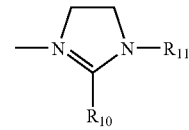

wherein $R_7$, $R_{11}$ and $R_{12}$ are independently selected from $C_1$-$C_{18}$ alkyl; $R_8$, $R_9$, $R_{10}$ and $R_{15}$ are independently selected from $C_8$-$C_{18}$ alkyl and $C_8$-$C_{18}$ alkenyl; and $R_{11}$ is selected from groups of formula —$CH_2CH_2OH$, —$CH_2CH_2NH_2$ and —$CH_2CH_2NHC(O)R_{15}$.

In another preferred aspect, n is 0.

In another preferred aspect, n is 0 and $R_1R_2R_3N$— and $R_4R_5R_6N$— are independently selected from groups of formula —$N(CH_3)_2R_8$;

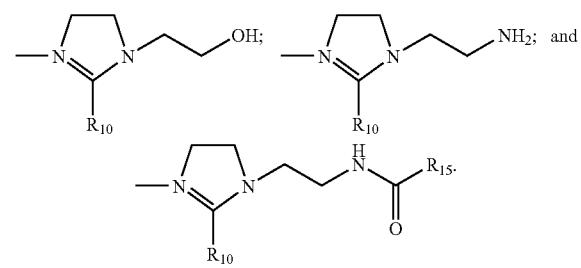

In another preferred aspect, n is 0 and $R_8$ is $C_8$-$C_{18}$ alkyl.
In another preferred aspect, n is 0 and $R_8$ is $C_8$-$C_{18}$ alkenyl.
In another preferred aspect, n is 0 and $R_{10}$ is $C_8$-$C_{18}$ alkenyl.
In another preferred aspect, n is 1.
In another preferred aspect, n is 1 and $R_1R_2R_3N$— and $R_4R_5R_6N$— are groups of formula —$N(CH_3)_2R_8$, —$N(CH_2CH_2OH)_3$, —$N(CH_2CH_3)_3$ or —$N(CH_3)_2CH_2CH_2OC(O)R_9$.

In another preferred aspect, the quaternary salts are selected from the group consisting of salts of formula

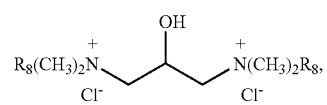

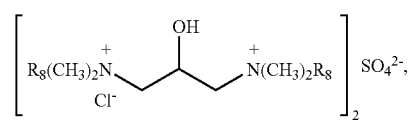

-continued

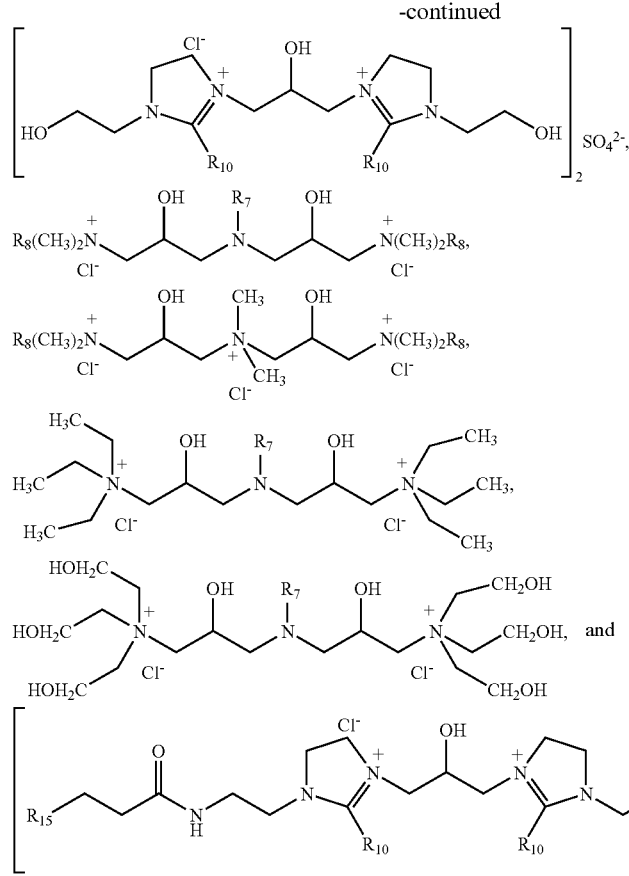

In another aspect, this invention is a composition for inhibiting corrosion and biofouling of metallic surfaces in contact with a fluid encountered in petroleum operations comprising one or more bis-quaternary ammonium salts as described above.

The bis-quaternary ammonium salts are preferably used in the form of a solution or dispersion in water and/or an organic solvent. Representative organic solvents includes alcohols such as methanol, ethanol, isopropanol, isobutanol, secondary butanol, glycols and aliphatic and aromatic hydrocarbons. The bis-quaternary ammonium salts may also be formulated with one or more mercaptans such as thiolacetic acid, 1,2-ethanedithiol, or preferably 2-mercaptoethanol. Typical compositions contain about 5 to about 70, preferably about 20 percent by weight of bisammonium quaternary salts.

The effective corrosion and biofouling inhibiting amount of bis-quaternary ammonium salts varies with the system in which the inhibitor is being used. Methods for monitoring the severity of corrosion and biofouling in different systems are well known, and may be used to decide the effective amount of bis-quaternary ammonium salts required in a particular situation. Typical effective doses of bis-quaternary ammonium salt range from about 5 to about 250 ppm although in certain instances doses of up to about 1,000 ppm or more may be required.

The bis-quaternary ammonium salts may also be formulated with other materials commonly used in corrosion inhibiting compositions including scale inhibitors, surfactants, and the like.

The bis-quaternary ammonium salts of this invention have been shown to be effective for inhibiting biofouling and mild steel corrosion as well as corrosion of other types of metallurgy in hydrocarbon, oil/brine mixtures and aqueous systems under a variety of conditions.

They can be used in primary, secondary and tertiary oil recovery and be added in a manner known per se. In a preferred method of this invention, the bis-quaternary ammonium salt is added at any point in the flow line upflow from the point at which corrosion prevention and inhibition of biofouling is desired.

Another technique in primary oil recovery where they can be used is the squeeze treating technique, whereby they are injected under pressure into the producing formation, are adsorbed on the strata and desorbed as the fluids are produced. They can further be added in the water flooding operations of secondary oil recovery as well as be added to pipelines, transmission lines and refinery units.

The foregoing may be better understood by reference to the following examples, which are presented for purposes of illustration and are not intended to limit the scope of the invention.

EXAMPLE 1

Preparation of a Representative Bis-Quaternary Ammonium Salt Where n=0

N,N-Dimethyldodecylamine (2.87 kg, 13.45 mol) and methanol (0.97 kg, 1.22 L) are combined in a three-neck 12-L flask fitted with a mechanical stirring device, a thermometer, and an addition funnel. The mixture is stirred at ambient temperature and 95% sulfuric acid (186 mL, 3.36 mol) is added via the addition funnel. The addition requires twelve minutes as the reaction temperature increases from 22.3 to 63.1° C. Five minutes later the temperature had dropped to 61.4° C., and epichlorohydrin (515 mL, 6.60 mol) is added to the reaction over thirty minutes. The temperature drops to 56.6° C. during the first fifteen minutes of the addition and then climbs to 63.3° C. during the final fifteen minutes. Ten minutes later, the mixture is heated at 80° C. for five hours. The resulting solution is cooled and directly formulated into corrosion inhibitor mixtures as approximately 20% solutions in water and methanol.

EXAMPLE 2

Preparation of a Representative Bis-Quaternary Ammonium Salt Where n=1

Oleylamine (1.13 kg, 4.23 mol) and methanol (2.04 kg, 2.58 L) are combined in a three-neck 12-L flask fitted with a mechanical stirring device, a thermometer, and an addition funnel. The mixture is cooled with an ice bath to about 0° C. Epichlorohydrin (645 mL, 8.25 mol) is slowly added over ninety minutes from the addition funnel to the flask. The resulting mixture is stirred for six additional hours as it warms to ambient temperature. N,N-Dimethyldodecylamine (1.89 kg, 8.46 mol) is then added over twenty minutes and the mixture is heated to 80° C. for six hours. The resulting solution is cooled and directly formulated into corrosion inhibitor mixtures as approximately 20% solutions in water and methanol.

EXAMPLE 3

Wheelbox Test

Cleaned and pre-weighed coupons are put into bottles containing a mixture of brine (180 mL), and hydrocarbon (LVT 200, 20 mL) and 500 ppm of acetic acid and the resulting mixture is purged with carbon dioxide. An increasing amount of tested inhibitor (5, 10, 25 and 50 ppm) is added into the bottles, the air space in the bottles is purged with $CO_2$ mixture and immediately capped to avoid air contamination. In addition to those bottles that are dosed with inhibitor, three bottles remain untreated. The complete set of capped test bottles is set on the rotating wheel, and run for 24 hours at 176° F. On conclusion of the test, the bottles are removed and allowed to cool to room temperature. The bottles are then uncapped and the coupons are removed, cleaned, dried and re-weighed. Corrosion rate and protection efficiency are then calculated by comparing the mass loss of inhibited coupons to those of the blanks.

Comparative test results for representative bis-quaternary ammonium salts prepared according to the methods of Examples 1 and 2 and a commercially available quaternary ammonium salt are shown in Table 1.

TABLE 1

Wheelbox Test - Actives Only
Percent Protection

| Inhibitor | 5 | 10 | 25 | 50 ppm |
|---|---|---|---|---|
| Blank | 0 | 0 | 0 | 0 |
| Commercial A | 13 | 55 | 83 | 89 |
| Example 1 | 65 | 81 | 92 | 91 |
| Example 2 | 21 | 73 | 86 | 89 |

As shown in Table 1, the bis-quaternary ammonium salts of this invention outperform the current commercial standard.

EXAMPLE 4

Field Trial.

Field corrosion rate data are obtained from a production line in an Alaskan field that is equipped with high sensitivity electrical resistance MicroCor probes (Rohrback Cosasco Systems, Santa Fe Springs, Calif.). The sensing element of the probe, positioned into gas/oil/brine multiphase flow, reads a cumulative metal loss that is transformed into corrosion rate. Once an uninhibited corrosion rate baseline has been established, corrosion inhibitor formulations are incrementally injected upstream of the probe over a period of thirty hours. The resulting drop in corrosion rates are used to calculates protection efficiency and establish the relative rankings of corrosion inhibitor formulations.

Comparative test results for representative bis-quaternary ammonium salts prepared according to the methods of Examples 1 and 2, a commercially available quaternary ammonium salt and a commercially available alkylbenzyldimethylammonium salt are shown in Table 2.

TABLE 2

Field Performance - Corrosion Inhibitor Formulations
Percent Protection

| Inhibitor | 3 | 6 | 11 | 22 | 44 ppm |
|---|---|---|---|---|---|
| Commercial A | 63.1 | 77.0 | 81.8 | 91.8 | 92.7 |
| Commercial B | 21.5 | 41.3 | 48.2 | 64.9 | 92.7 |
| Example 1 | 60.5 | 87.6 | 89.8 | 91.8 | 98.3 |
| Example 2 | 76.2 | 96.2 | 95.3 | 97.8 | 98.0 |

As shown in Table 2, the bis-quaternary ammonium salts of this invention outperform the current commercial standards.

EXAMPLE 5

Biostatic Assay.

The biostatic properties of representative bis-quaternary ammonium salts are characterized according to the current NACE standard—NACE TMO194094. Viable organisms are cultured from aqueous field samples in iron-rich media purchased from Commercial Microbiology (Houston, Tex.). Stock solutions of the viable organisms in ferrous media are serially diluted in triplicate. Black iron sulfide precipitates indicate micobial growth (of sulfate-reducing bacteria). Clear media solutions indicate complete cell death. Pure media solutions are used as controls and compared against media spiked with 5 to 500 ppm of a test compound. Additives that require increased dilutions to attain complete cell death promote bacterial growth, relative to the standard. Those compounds that required fewer dilutions are relatively biostatic.

Comparative test results for representative bis-quaternary ammonium salts prepared according to the methods of Examples 1 and 2 and commercially available quaternary ammonium salts A and B are shown in Table 3.

TABLE 3

Biostatic Activity - Actives Only
log reduction of SRB growth

| Inhibitor | 10 | 25 | 100 ppm |
|---|---|---|---|
| Commercial A | 0.2 | 6 | 6 |
| Commercial B | 0 | 3.4 | 6 |
| Example 1 | 6 | 6 | 6 |
| Example 2 | 0 | 6 | 6 |

As shown in Table 3, a representative corrosion inhibitor prepared according to the method of Example 1 outperforms both commercially available quaternary ammonium salts. The representative corrosion inhibitor maintains a log reduction of 6 (zero colonies grew) at concentrations as low as 10 ppm while the commercial treatment A maintains a log reduction of 6 at concentrations only as low as 25 ppm. At 10 ppm, commercial treatment A shows virtually no biostatic capability. Commercial treatment B requires even higher (100 ppm) concentrations to inhibit bacterial growth.

Changes can be made in the composition, operation, and arrangement of the method of the invention described herein without departing from the concept and scope of the invention as defined in the claims.

The invention claimed is:

1. A method of inhibiting corrosion and biofouling of metallic surfaces in contact with a fluid encountered in petroleum operations comprising adding to the fluid up to about 1,000 ppm of one or more bis-quaternary ammonium salts of formula

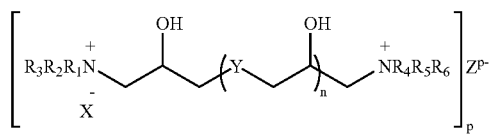

wherein Y is a group of formula $NR_{11}R_{12}^+X^-$ or $NR_7$; n is 1; p is 1 or 2; r and q are independently 2, 3 or 4; X is an anionic counterion, Z is an anionic counterion, and $R_1R_2R_3N—$ and $R_4R_5R_6N—$ are independently selected from groups of formula $—N(R_{13})_2R_8$, $—N(R_{14})_3$, $—N(R_{13})_3$, $—N(R_{13})_2(CH_2)_qOC(O)R_9$,

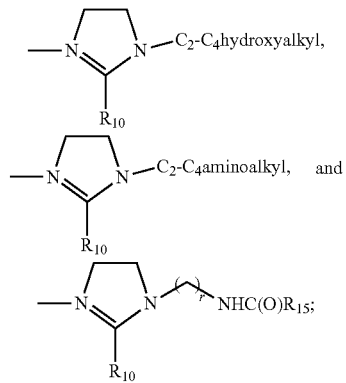

wherein $R_7$, $R_{11}$ and $R_{12}$ are independently selected from $C_1-C_{18}$ alkyl; $R_8$, $R_9$, $R_{10}$ and $R_{15}$ are independently selected from $C_8-C_{18}$ alkyl and $C_8-C_{18}$ alkenyl; $R_{13}$ is $C_1-C_4$ alkyl; $R_{14}$ is $C_2-C_4$ hydroxyalkyl; and wherein said petroleum operation is primary, secondary, and/or tertiary oil recovery.

2. The method of claim 1 wherein $R_1R_2R_3N—$ and $R_4R_5R_6N—$ are independently selected from groups of formula $—N(CH_3)_2R_8$, $—N(CH_2CH_2OH)_3$, $—N(CH_2CH_3)_3$, $—N(CH3)_2CH_2CH_2OC(O)R_9$,

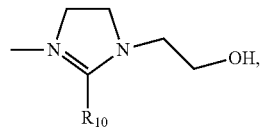

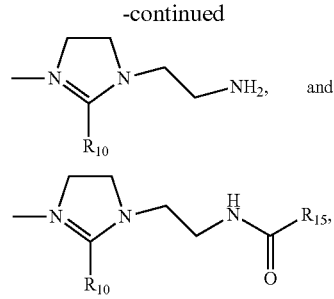

wherein $R_7$, $R_{11}$ and $R_{12}$ are independently selected from $C_1-C_{18}$ alkyl; $R_8$, $R_9$, $R_{10}$ and $R_{15}$ are independently selected from $C_8-C_{18}$ alkyl and $C_8-C_{18}$ alkenyl; and $R_{11}$ is selected from groups of formula $—CH_2CH_2OH$, $—CH_2CH_2NH_2$ and $—CH_2CH_2NHC(O)R_{15}$.

3. The method of claim 2 wherein $R_1R_2R_3N—$ and $R_4R_5R_6N—$ are independently selected from groups of formula $—N(CH_3)_2R_8$;

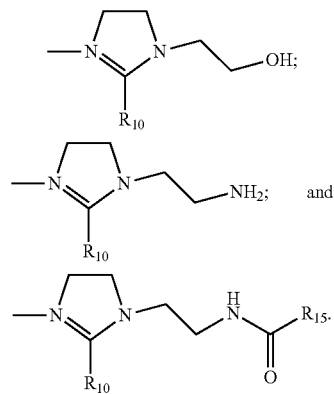

4. The method of claim 3 wherein $R_8$ is $C_8-C_{18}$ alkyl.

5. The method of claim 3 wherein $R_8$ is $C_8-C_{18}$ alkenyl.

6. The method of claim 3 wherein $R_{10}$ is $C_8-C_{18}$ alkenyl.

7. The method of claim 1 wherein n is 1.

8. The method of claim 7 wherein $R_1R_2R_3N—$ and $R_4R_5R_6N—$ are groups of formula $—N(CH_3)_2R_s$, $—N(CH_2CH_2OH)_3$, $—N(CH_2CH_3)_3$ or $—N(CH_3)_2CH_2CH_2OC(O)R_9$.

9. The method of claim 1 wherein the bis-quaternary ammonium salts are selected from the group consisting of salts of formula

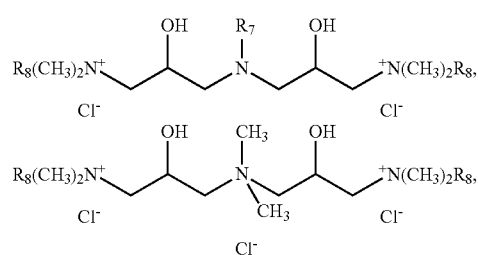

-continued
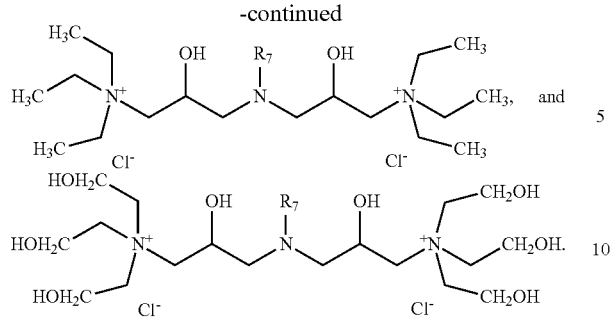
10. The method of claim 1 wherein the fluid is an oil field fluid comprising oil and water.
11. The method of claim 1 wherein Z is chloride or sulfate.
12. The method of claim 1 wherein Z is chloride.
* * * * *